US00PP36723P2

(12) United States Plant Patent
Carrella

(10) Patent No.: US PP36,723 P2
(45) Date of Patent: Jun. 3, 2025

(54) ***CALIBRACHOA* PLANT NAMED 'KLECA23916'**

(50) Latin Name: ***Calibrachoa* sp.**
Varietal Denomination: KLECA23916

(71) Applicant: KLEMM + SOHN GMBH & CO. KG, Stuttgart (DE)

(72) Inventor: Angelo Carrella, Palma Campania (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/761,218

(22) Filed: Jul. 1, 2024

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413

CPC . A01H 5/02; A01H 5/00; A01H 6/821; A01H 6/82

See application file for complete search history.

(56) References Cited

PUBLICATIONS

Allegro Archives retrieved on Oct. 21, 2024 at https://archiwum-allegro-pl.translate.goog/oferta/calibrachoa-m-fam-neo-summer-joy-milion-dzwonkow-i14393539556.html?_x_tr_sl=pl&_x_tr_tl=en&_x_tr_hl=en&_x_tr_pto=sc, 4 pp. (Year: 2024).*

Selecta One MiniFamous Neo retrieved on Oct. 21, 2024 at https://selecta-one.com/en/assortment/overview/minifamous-neo?series=6614&cHash=15807d5967f6b6e173cfb20326c452b9, 17 pp. (Year: 2024).*

* cited by examiner

*Primary Examiner* — June Hwu
(74) *Attorney, Agent, or Firm* — Weatherly IP Solutions LLC; James M. Weatherly; Karen Bechtold

(57) ABSTRACT

A new *Calibrachoa* plant particularly distinguished by having a red-purple flower color with yellow stripe, vigorous growth habit; and a semi-trailing plant habit, is disclosed.

1 Drawing Sheet

Genus and species: *Calibrachoa* sp.
Variety denomination: 'KLECA23916'.

BACKGROUND OF THE NEW PLANT

The present invention comprises a new and distinct variety of *Calibrachoa*, botanically known as *Calibrachoa* sp., and hereinafter referred to by the variety name 'KLECA23916'. 'KLECA23916' originated from a controlled-cross between the proprietary female *Calibrachoa* variety 'CA-2018-2630' (unpatented) and the male *Calibrachoa* variety 'CA-2018-3002' (unpatented).

In August 2018, two *Calibrachoa* parental lines, the female variety 'CA-2018-2630' and the male variety 'CA-2018-3002' were crossed via a controlled-cross in Stuttgart, Germany and seeds were obtained. The seeds were sown and plants were grown for evaluation. A plant line was selected in May 2019 and subsequently named 'KLECA23916'. In May 2019, 'KLECA23916' was first vegetatively propagated by cuttings in Stuttgart, Germany. 'KLECA23916' was found to reproduce true to type in successive generations of asexual propagation via cuttings.

SUMMARY

The following are the most outstanding and distinguishing characteristics of this new variety when grown under normal horticultural practices in Stuttgart, Germany.

1. Red-purple flower color with a yellow stripe;
2. Vigorous growth habit; and
3. Semi-trailing plant habit.

DESCRIPTION OF THE PHOTOGRAPH

This new *Calibrachoa* plant is illustrated by the accompanying photograph which shows a close-up of the whole plant. The photograph is of a 11-week-old-plant grown in in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLECA23916'. The data which define these characteristics were collected from asexual reproductions carried out in Stuttgart, Germany. Data was collected on 15-week old plants after transplant in Latina, Italy. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female.*—CA-2018-2630 (unpatented).
*Male.*—CA-2018-3002 (unpatented).

Plant description:
*Life cycle*.—Annual.
*Form*.—Short-lived subshrub.
*Habit*.—Semi-trailing.
*Height* (*from soil line to top of foliage*).—10.8 cm.
*Spread*.—32.1 cm.
Propagation:
*Type cuttings*.—Tip cutting.
*Time to produce a rooted cutting*.—3 weeks.
Stems:
*Stem color*.—RHS 144 C.
*Pubescence*.—Present.
*Pubescence color*.—RHS 155A.
*Stem diameter*.—0.12 cm.
*Stem length*.—From soil line to first node: 1.8 cm. Total length: 16.8 cm.
*Internode length*.—1.3 cm.
Leaves:
*Arrangement*.—Alternate.
*Shape*.—Obovate.
*Apex*.—Obtuse.
*Base*.—Acute.
*Margin*.—Ciliate.
*Surface pubescence*.—Upper and lower surfaces are smooth.
*Pubescence color*.—RHS 155A.
*Venation color*.—Upper surface: RHS 144B. Lower surface: RHS 144B.
*Venation pattern*.—Upper and lower surfaces are pinnate.
*Length*.—3.1 cm (mature leaves).
*Width*.—1.3 cm (mature leaves).
*Color*.—Upper surface: RHS 138A. Lower surface: RHS 138B.
*Fragrance*.—Absent.
Flowers:
*Flowering habit*.—Single flower.
*Flower type*.—Single.
*Flowering requirements*.—A minimum amount of 10.5 hours per day of sunlight is required.
*Duration of flowers*.—7 to 10 days.
*Corolla*.—Smooth (both upper and lower surfaces).
*Shape*.—Funnel form.
*Corolla lobing*.—Strong.
*Fragrance*.—Absent.
*Upper surface flower vein conspicuousness*.—Weak.
Flower buds:
*Surface*.—Pubescent.
*Length*.—2.0 cm.
*Diameter*.—0.4 cm.
*Shape*.—Irregular to oblong.
*Color*.—RHS 61C (top buds) 145C (base buds).
Pedicel:
*Length*.—1.9 cm.
*Diameter*.—Less than 0.1 cm.
*Color*.—RHS 144C.
*Texture*.—Pubescent.
*Anthocyanin color*.—Present.

Flower description:
*Flower depth*.—2.3 cm.
*Flower tube length*.—1.4 cm.
*Flower tube diameter*.—0.9 cm.
*Flower diameter*.—3.8 cm.
Sepals:
*Shape*.—Ovate.
*Apex*.—Obtuse.
*Margin*.—Ciliate.
*Length*.—1.0 cm.
*Diameter*.—0.35 cm.
*Sepal color*.—Upper surface: RHS 138A. Lower surface: RHS 138B.
Petals:
*Shape*.—Obcordate.
*Length*.—1.4 cm.
*Apex*.—Obtuse.
*Margin*.—Entire.
*Base*.—Fuse in the tube.
*Pubescence*.—Absent on both upper and lower petal surfaces.
*Flower lobing*.—Strong, 5 lobes per flower.
*Lobe length*.—1.5 cm.
*Lobe width*.—1.4 cm.
*Color*.—Lobe color: Upper surface: RHS 61C main color and RHS 4B stripes. Lower surface: RHS N57C main color and RHS 4D stripes. Corolla tube color: Inner: RHS 7A. Outer: RHS 2A.
*Secondary color on upper lobe surface*.—Irregular distribution of RHS 4B.
*Secondary color on lower lobe surface*.—Irregular distribution of RHS 4D.
*Fragrance*.—Absent.
Reproductive organs:
*Stamen number*.—5.
*Stamen color*.—Anther color: RHS 13B. Filament color: RHS 2C. Pollen color: RHS 12A.
*Ovary*.—Placenta arrangement: ovate. Pistil number: 1.Pistil length: 0.8 cm. Stigma color: RHS 144B. Style length: 0.7 cm. Style color: RHS 144C.
Fruit/seed set: None observed.
Disease/insect resistance: No pests and disease were observed.

COMPARISON WITH PARENTAL LINES AND KNOWN VARIETY

'KLECA23916' is distinguished from its parents as described in Table 1 and Table 2:

TABLE 1

Comparison with Female Parental Line

| Trait | Variety 'KLECA23916' | Female parent 'CA-2018-2630' |
|---|---|---|
| Vigor (measured on a scale of 1 to 9, which 9 being high vigor and 1 being low vigor) | Vigorous growth, with a value of 8 on the vigor scale. | Less vigorous than Variety 'KLECA23916' with a value of 6 on the vigor scale. |

TABLE 2

| Comparison with Male Parental Line | | |
|---|---|---|
| Trait | Variety 'KLECA23916' | Male Parent 'CA-2018-3002' |
| Earliness | 38 days from potting to flowering | 48 days from potting to flowering |

'KLECA23916' is most similar to the *Calibrachoa* plant named 'KLECA16006' (U.S. Plant Pat. No. 29,433). Differences between the two varieties are described in Table 3:

TABLE 3

| Comparison with Similar Variety | | |
|---|---|---|
| Trait | Variety 'KLECA23916' | Commercial line 'KLECA16006' |
| Main flower petal color | Red- purple color with yellow stripe | Pink color with white stripes |

I claim:

1. A new and distinct cultivar of *Calibrachoa* Plant Named 'KLECA23916' as shown and described herein.

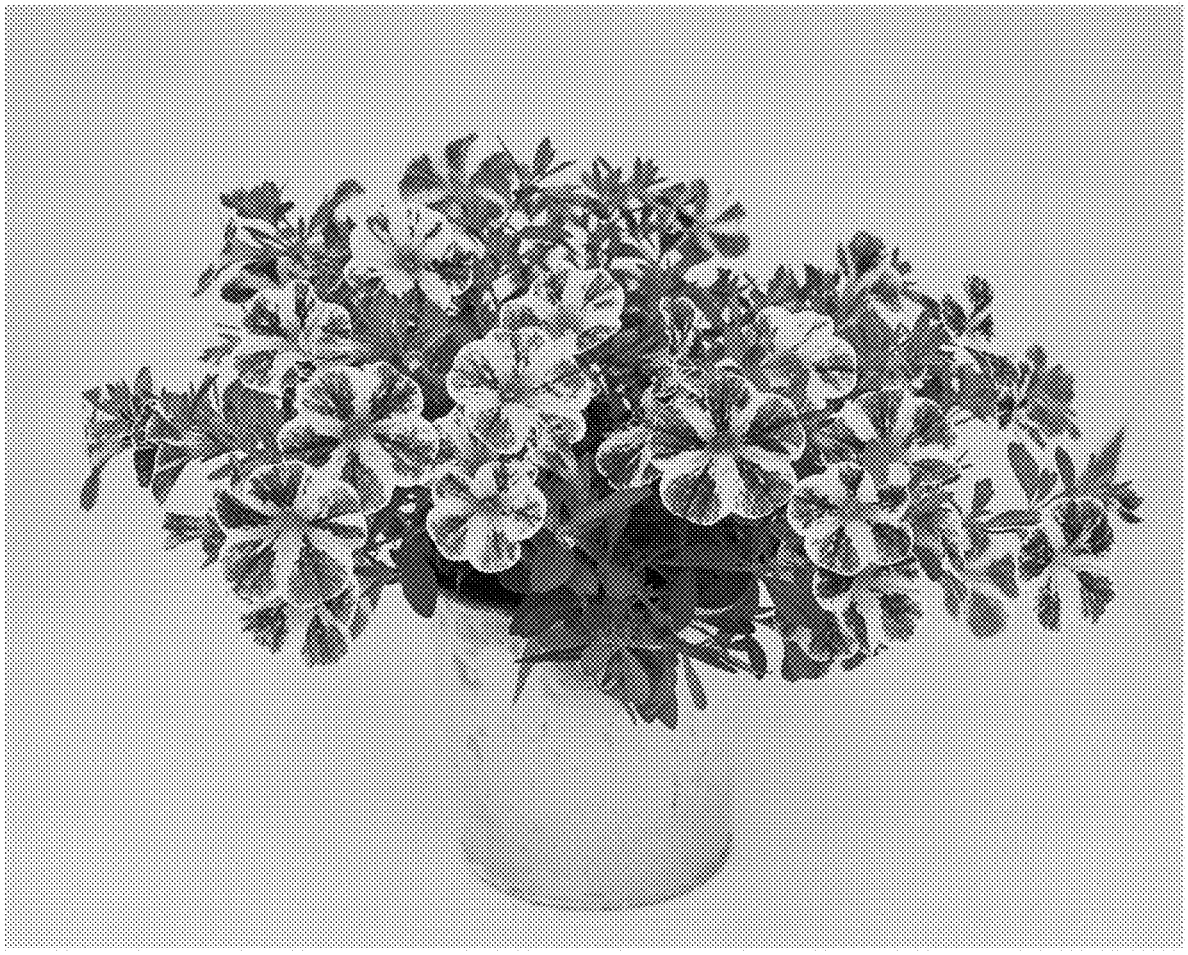

* * * * *